United States Patent
Levesque et al.

(10) Patent No.: US 9,600,083 B2
(45) Date of Patent: Mar. 21, 2017

(54) SYSTEMS AND METHODS TO GENERATE HAPTIC FEEDBACK FOR SKIN-MEDIATED INTERACTIONS

(71) Applicant: IMMERSION CORPORATION, San Jose, CA (US)

(72) Inventors: Vincent Levesque, Montreal (CA); Juan Manuel Cruz-Hernandez, Montreal (CA)

(73) Assignee: Immersion Corporation, San Jose, CA (US)

( * ) Notice: Subject to any disclaimer, the term of this patent is extended or adjusted under 35 U.S.C. 154(b) by 0 days.

(21) Appl. No.: 14/331,592

(22) Filed: Jul. 15, 2014

(65) Prior Publication Data
US 2016/0019762 A1    Jan. 21, 2016

(51) Int. Cl.
| | | |
|---|---|---|
| *G06F 3/041* | (2006.01) | |
| *G06F 3/01* | (2006.01) | |
| *G06F 3/0488* | (2013.01) | |

(52) U.S. Cl.
CPC .............. *G06F 3/018* (2013.01); *G06F 3/016* (2013.01); *G06F 3/041* (2013.01); *G06F 3/04886* (2013.01)

(58) Field of Classification Search
CPC ...... A61H 2201/165; A61H 2201/1652; A61H 2201/1654; A61H 2201/5058; G06F 3/016; G06F 3/018; G06F 3/011; G06F 3/014; G06F 3/017; G06F 3/041; G06F 3/0414; G06P 3/016; G06P 3/0488; A61N 1/0456
See application file for complete search history.

(56) References Cited

U.S. PATENT DOCUMENTS

| | | | | |
|---|---|---|---|---|
| 8,740,825 B2* | 6/2014 | Ehrenreich | .............. | A61H 1/00 381/151 |
| 8,988,373 B2* | 3/2015 | Thorn | ..................... | G06F 3/011 345/173 |
| 8,994,672 B2* | 3/2015 | Thorn | ..................... | G06F 3/011 345/173 |
| 9,024,870 B2* | 5/2015 | Kim | ..................... | G06F 1/1626 345/156 |
| 2011/0155044 A1* | 6/2011 | Burch | ..................... | G06F 3/016 116/205 |
| 2012/0056825 A1* | 3/2012 | Ramsay | .................. | G06F 3/016 345/173 |

(Continued)

FOREIGN PATENT DOCUMENTS

EP        2 256 592 A1    12/2010

OTHER PUBLICATIONS

Gustafson, S., et al., "Imaginary Phone: Learning Imaginary Interfaces by Transferring Spatial Memory from a Familiar Device," UIST'11, Oct. 16-19, 2011, Santa Barbara, CA, USA, pp. 283-292.

(Continued)

*Primary Examiner* — Van Trieu
(74) *Attorney, Agent, or Firm* — Merchant & Gould P.C.

(57) ABSTRACT

A system includes a sensor configured to sense an input at a skin surface, a processor configured to receive an output signal from the sensor and generate a haptic control signal based on the output signal, and a haptic output device configured to generate a haptic effect based on the haptic control signal.

23 Claims, 9 Drawing Sheets

(56) References Cited

U.S. PATENT DOCUMENTS

| | | | | |
|---|---|---|---|---|
| 2012/0062491 | A1* | 3/2012 | Coni | G06F 3/016 345/173 |
| 2013/0257757 | A1* | 10/2013 | Kim | G06F 3/165 345/173 |
| 2013/0345606 | A1* | 12/2013 | Ehrenreich | A61H 1/00 601/46 |
| 2014/0002390 | A1* | 1/2014 | Lee | G06F 3/041 345/173 |
| 2014/0004906 | A1* | 1/2014 | Chi | H04B 1/38 455/566 |
| 2014/0059427 | A1* | 2/2014 | Dombrowski | G06F 3/016 715/701 |
| 2014/0181686 | A1* | 6/2014 | Shin | G06F 3/1454 715/748 |
| 2014/0240223 | A1* | 8/2014 | Lake | G08C 17/02 345/156 |
| 2014/0296935 | A1* | 10/2014 | Ferree | A61N 1/36021 607/46 |
| 2015/0035658 | A1* | 2/2015 | Provancher | G08B 6/00 340/407.1 |
| 2015/0185849 | A1* | 7/2015 | Levesque | G06F 3/016 340/636.1 |

OTHER PUBLICATIONS

Harrison, C., et al., "Skinput: Appropriating the Body as an Input Surface," CHI 2010: Computing on the Body, Apr. 10-15, 2010, Atlanta, GA, USA, pp. 453-462.

Ogata, M., et al., "SenSkin: Adapting Skin as a Soft Interface," UIST'13, Oct. 8-11, 2013, St. Andrews, UK, pp. 539-543.

Chan, L., et al., "FingerPad: Private and Subtle Interaction Using Fingertips," UIST'13, Oct. 8-11, 2013, St. Andrews, UK, pp. 255-260.

Lopes, P., et al., "Muscle-Propelled Force Feedback: Bringing Force Feedback to Mobile Devices," CHI 2013: Changing Perspectives, Paris, France, 2013, pp. 2577-2580.

Tamaki, E., et al., "PossessedHand: Techniques for Controlling Human Hands using Electrical Muscles Stimuli," CHI 2011, May 7-12, 2011, Vancouver, BC, Canada, pp. 543-552.

Lissermann, R., et al., "EarPut: Augmenting Behind-the-Ear Devices for Ear-based Interaction," CHI 2013: Changing Perspectives, Paris, France, 2013, pp. 1323-1328.

Serrano, M., et al., "Exploring the Use of Hand-To-Face Input for Interacting with Head-Worn Displays," CHI 2014, One of a CHind, Toronto, ON, Canada, 2014, pp. 3181-3190.

Extended European Search Report as issued in European Patent Application No. 15176667.2, dated Nov. 25, 2015.

Makino, Y., et al., "Paired Vibratory Stimulation for Haptic Feedback," $4^{th}$ Augmented Human International Conference (AH'13), Mar. 7-8, 2013, pp. 47-50.

Nakatsuma, K., et al., "Touch Interface on Back of the Hand," SIGGRAPH '11: SIGGRAPH 2011 Emerging Technologies, Aug. 7-11, 2011, 1 page.

Weiss, M., et al., "FingerFlux: Near-surface Haptic Feedback on Tabletops," Proceedings of the $24^{th}$ Annual ACM Symposium on User Interface Software and Technology, Oct. 16-19, 2011, pp. 615-620.

Tamaki, E., et al., "A Half-Implant Device on Fingernails," CHI 2014, One of a CHInd, pp. 1447-1452.

* cited by examiner

SYSTEMS AND METHODS TO GENERATE HAPTIC FEEDBACK FOR SKIN-MEDIATED INTERACTIONS

FIELD

The present invention relates to systems and methods to generate haptic feedback for skin-mediated interactions.

BACKGROUND

Several research projects have proposed using a person's skin as an interaction surface for providing input to an electronic device. For example, as reported at the Association for Computing Machinery ("ACM") Conference on Human Factors in Computing Systems during Apr. 10-15, 2010 in Atlanta, Ga. ("CHI 2010"), a technology called "Skinput," which uses different body locations (e.g., fingers, arms and forearms) as interaction surfaces, was introduced. The touch input on skin surfaces of the body locations is detected by measuring the propagation of vibrations on the skin caused by movement of a person's finger against the skin surface. As reported at the ACM symposium on the User Interface Software and Technology during Oct. 16-19, 2011 in Santa Barbara, Calif. ("UIST'11"), a palm of a user's hand may be used as an interaction surface, and a touch input on the user's palm is detected using a depth camera and image processing techniques.

As reported at the Association for Computing Machinery ("ACM") Symposium on User Interface Software and Technology during Oct. 8-11, 2013 in St. Andrews, United Kingdom ("UIST'13"), a technology called "FingerPad" makes it possible to use the skin of the fingerpad of a user's index finger as a touch surface against which the thumb can move and provide input via a pinch gesture. Tracking of the input is performed with magnetic trackers attached to the index finger and thumb. As also reported at UIST'13, a technology called "SenSkin" similarly uses the surface of the skin of a forearm of a user as an interaction surface, and tracking of a touch input on the skin of the forearm is performed using infrared sensors that detect deformation of the skin near two armbands wrapped around the forearm.

SUMMARY

It is desirable to add haptic feedback to such skin-mediated interactions so that the user knows the input provided to the skin surface is received by the electronic device.

According to an aspect of the present invention, there is provided a system that includes a sensor configured to sense an input at a skin surface; a processor configured to receive an output signal from the sensor and generate a haptic control signal based on the output signal; and a haptic output device configured to generate a haptic effect based on the haptic control signal.

In an embodiment, the sensor is configured to sense the input at the skin surface of a user of the system, and the haptic output device is configured to generate the haptic effect to the user of the system.

In an embodiment, the haptic output device is configured to be carried by a wearable device. In an embodiment, the wearable device includes a ring. In an embodiment, the wearable device includes a wristband or a bracelet.

In an embodiment, the haptic output device includes an actuator and the haptic effect comprises a vibration.

In an embodiment, the haptic output device includes at least one electrode connected to a power source.

In an embodiment, the haptic effect includes an electrotactile stimulation.

In an embodiment, the haptic effect includes muscle stimulation.

In an embodiment, the haptic output device includes a mechanical apparatus configured to stretch or pull the skin.

In an embodiment, the haptic output device includes a pair of electromagnets configured to cause attraction or repulsion of two interacting skin surfaces of the user.

In an embodiment, the haptic output device is configured to generate air vortices.

According to an aspect of the invention, there is provided a method that includes sensing an input from a user at a skin surface of the user; generating a haptic control signal based on the sensed input; and generating a haptic effect to the user with a haptic output device based on the haptic control signal.

In an embodiment, the haptic effect includes a vibration.

In an embodiment, the haptic effect includes an electrotactile stimulation.

In an embodiment, the haptic effect includes muscle stimulation.

In an embodiment, the haptic effect includes stretching or pulling the skin.

In an embodiment, the haptic effect includes causing attraction or repulsion of two interacting skin surfaces of the user.

In an embodiment, the haptic effect includes ultrasound or air vortices.

In an embodiment, the method includes reducing a sensitivity of the skin surface to the haptic effect.

In an embodiment, the sensitivity of the skin surface is reduced by applying a topical anesthetic to the skin surface before sensing the input from the user.

In an embodiment, the sensitivity of the skin surface is reduced by lowering the temperature of the skin surface.

In an embodiment, the sensitivity of the skin surface is reduced by applying vibrations to the skin surface before sensing the input from the user.

These and other aspects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

The components of the following Figures are illustrated to emphasize the general principles of the present disclosure and are not necessarily drawn to scale. Reference characters designating corresponding components are repeated as necessary throughout the Figures for the sake of consistency and clarity.

DETAILED DESCRIPTION

Figure 1:
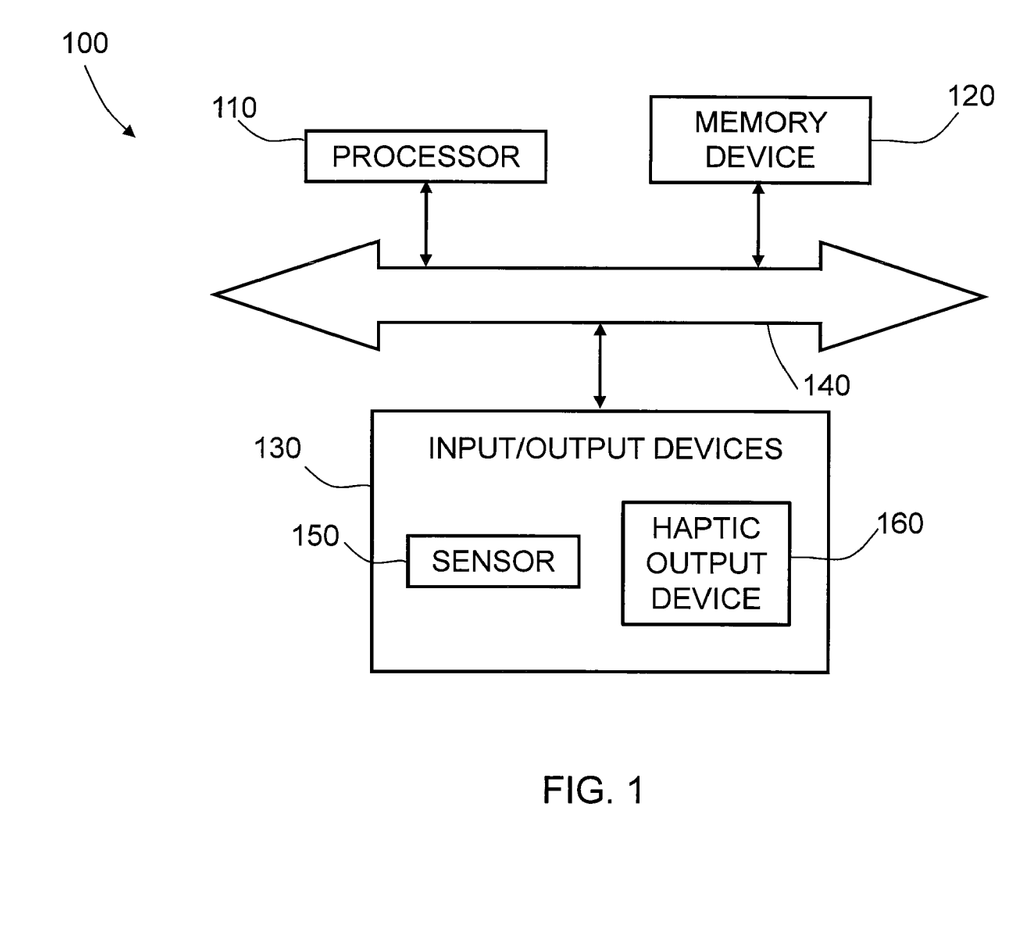
FIG. 1 schematically illustrates a system in accordance with an embodiment of the invention.

FIG. 1 is a schematic illustration of a system 100 in accordance with an embodiment of the invention. The system 100 may be part of an electronic device, such as a desktop computer, laptop computer, electronic workbook, electronic handheld device (such as a mobile phone, smart phone, gaming device, personal digital assistant ("PDA"), portable e-mail device, portable Internet access device, calculator, etc.), game controller, or wearable device such as a head mounted display, ring or wristband, for example. As illustrated, the system 100 includes a processor 110, a memory device 120, and input/output devices 130, which are interconnected via a bus 140. In an embodiment, the input/output devices 130 may include at least one sensor 150 and at least one haptic output device 160 and/or other human-computer interface devices.

The processor 110 may be a general-purpose or specific-purpose processor or microcontroller for managing or controlling the operations and functions of the system 100. For example, the processor 110 may be specifically designed as an application-specific integrated circuit ("ASIC") to control output signals to a driver of the input/output devices 130 to provide haptic effects. The processor 110 may be configured to decide, based on predefined factors, what haptic effects are to be generated based on a haptic signal received or determined by the processor 110, the order in which the haptic effects are generated, and the magnitude, frequency, duration, and/or other parameters of the haptic effects. The processor 110 may also be configured to provide streaming commands that can be used to drive the haptic output device 160 for providing a particular haptic effect. In some embodiments, the processing device 110 may actually include a plurality of processors, each configured to perform certain functions within the electronic device 100. The processor 110 is described in further detail below.

The memory device 120 may include one or more internally fixed storage units, removable storage units, and/or remotely accessible storage units. The various storage units may include any combination of volatile memory and non-volatile memory. The storage units may be configured to store any combination of information, data, instructions, software code, etc. More particularly, the storage units may include haptic effect profiles, instructions for how the haptic output device 160 of the input/output devices 130 are to be driven, or other information for generating haptic effects.

The bus 140 may be configured to allow signal communication between the various components of the system 100 and also to access information from remote computers or servers through, for example, a network. The network may include any one or more of, for instance, the Internet, an intranet, a PAN (Personal Area Network), a LAN (Local Area Network), a WAN (Wide Area Network), a SAN (Storage Area Network), a MAN (Metropolitan Area Network), a wireless network, a cellular communications network, a Public Switched Telephone Network, and/or other network.

The sensor 150 may be configured as any suitable input device configured to sense movement of, for example, a user's digit, i.e. finger, against a surface of the user's skin, as described in further detail below. The sensor 150 may sense the presence of a person's skin through capacitive, resistive, or inductive coupling, but is not limited to those techniques. In an embodiment, the sensor 150 may comprise an electromagnetic sensor, a capacitive sensor and/or a bio-acoustic sensor. In an embodiment, the sensor 150 may include a depth camera and processor for image processing the images captured by the depth camera. Further embodiments of the sensor 150 are described below.

The haptic output device 160 is configured to provide haptic feedback to the user of the system 100. Particularly, the haptic output device 160 may provide haptic feedback to the user's digit to impose a haptic effect as confirmation of the input, as described in further detail below. The haptic effects may be used to enhance the user experience when interacting with the system 100.

The haptic effects may be created with any of the methods of creating haptics, such as electrostatic or ultrasonic friction, deformation, vibration, kinesthetic sensations, etc. In an embodiment, the haptic output device 160 may include non-mechanical or non-vibratory devices such as those that use electrostatic friction ("ESF"), ultrasonic surface friction ("USF"), or those that induce acoustic radiation pressure with an ultrasonic haptic transducer, or those that use a haptic substrate and a flexible or deformable surface, or those that provide projected haptic output such as a puff of air using an air jet, and so on. In an embodiment, the haptic output device 160 may include an actuator, for example, an electromagnetic actuator such as an Eccentric Rotating Mass ("ERM") in which an eccentric mass is moved by a motor, a Linear Resonant Actuator ("LRA") in which a mass attached to a spring is driven back and forth, or a "smart material" such as piezoelectric materials, electro-active polymers or shape memory alloys, a macro-composite fiber actuator, an electro-static actuator, an electrotactile actuator, and/or another type of actuator that provides a physical feedback such as a haptic (e.g., vibrotactile) feedback. Multiple haptic output devices 160 may be used to generate different haptic effects, which may be used to create a wide range of effects such as textures, button clicks, state changes, etc.

Figure 2:
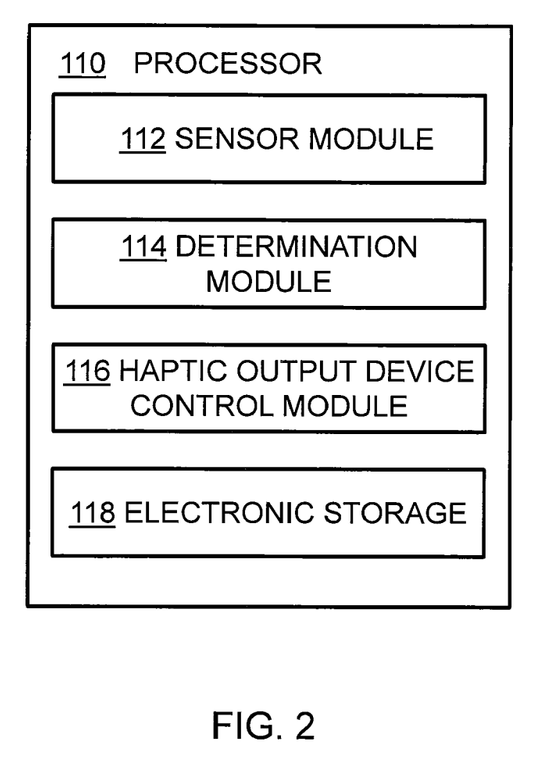
FIG. 2 schematically illustrates a processor of the system of FIG. 1.

FIG. 2 illustrates an embodiment of the processor 110 in more detail. The processor 110 may be configured to execute one or more computer program modules. The one or more computer program modules may include one or more of a sensor module 112, a determination module 114, a haptic output device control module 116, and/or other modules. The processor 110 may also include electronic storage 118, which may be the same as the memory device 120 or in addition to the memory device 120. The processor 110 may be configured to execute the modules 112, 114, and/or 116 by software, hardware, firmware, some combination of software, hardware, and/or firmware, and/or other mechanisms for configuring processing capabilities on processor 110.

It should be appreciated that although modules 112, 114, and 116 are illustrated in FIG. 2 as being co-located within a single processing unit, in embodiments in which the processor 110 includes multiple processing units, one or more of modules 112, 114, and/or 116 may be located remotely from the other modules. The description of the functionality provided by the different modules 112, 114, and/or 116 described below is for illustrative purposes, and is not intended to be limiting, as any of the modules 112, 114, and/or 116 may provide more or less functionality than is described. For example, one or more of the modules 112, 114, and/or 116 may be eliminated, and some or all of its functionality may be provided by other ones of the modules 112, 114, and/or 116. As another example, the processor 110 may be configured to execute one or more additional modules that may perform some or all of the functionality attributed below to one of the modules 112, 114, and/or 116.

The sensor module 112 is configured to receive an input signal from the sensor 150 that is generated when the sensor 150 detects a user input at a skin surface of a user of the system. In an embodiment, the skin surface may be of the same user providing the user input. In an embodiment, the skin surface may be of a different user of the system than the user providing the user input. The user input may be in the form of a single touch, as if pressing a virtual button on the interaction surface, multiple touches and/or a touch gesture(s). The sensor module 112 is also configured to send a signal to the determination module 114 for further processing.

The determination module 114 is configured to determine what type of input is intended by the user, what type of action is to be taken by the system 100 according to the input, and what type of haptic feedback is to be generated by the haptic output device 160. In an embodiment, the user may provide a particular gesture to the interaction skin surface that indicates that the user would like the system 100 to perform a particular action, such as for example initiating a phone call. The determination module 114 may be programmed with a library of predetermined gestures so that when the user touches a particular location on the surface or provides a gesture to the surface, the determination module 114 may determine a corresponding output. In addition, the determination module 114 may also output a signal to the haptic output device control module 116 so that a suitable haptic effect may be provided to the user.

The haptic output device control module 116 is configured to determine the haptic effect to be generated by the haptic output device 160, based on the signal generated by the determination module 114. Determining the haptic effect may include determining one or more parameters that include an amplitude, frequency, duration, etc., of the haptic effect that will provide the desired effect to the user.

Returning to FIG. 1, in an embodiment, the sensor 150 may be configured to be mounted to a user's finger and thumb such that the skin surface of the user's finger functions as a touch pad and the user's thumb functions as a touch stylus. Details of such an embodiment of the sensor 150 are provided in the article "FingerPad: Private and Subtle Interaction Using Fingertips" by Liwei Chan, et al., UIST'13, Oct. 6-9, 2013, pp. 255-260, which is incorporated herein by reference in its entirety.

In an embodiment, the sensor 150 may be configured to be mounted to a user's forearm and include two armbands that are spaced from each other such that the skin surface between the armbands may be used as a touch input surface. Details of such an embodiment of the sensor 150 are provided in the article "SenSkin: Adapting Skin as a Soft Interface" by Masa Ogata, et al., UIST'13, Oct. 8-11, 2013 at pp. 539-543, which is incorporated herein by reference in its entirety.

In an embodiment, the sensor 150 may be configured to be mounted to the user's arm, such as at the user's forearm, or to one or more fingers, and include a plurality of vibration sensors attached to a wearable device, such as an armband, a wristband, or a ring. Details of such an embodiment of the sensor 150 are provided in the article "Skinput: Appropriating the Body as an Input Surface" by Chris Harrison, et al., CHI 2010, Apr. 10-15, 2010, pp. 453-462, which is incorporated herein by reference in its entirety.

In an embodiment, the sensor 150 may include a camera, such as a depth camera, that is configured to capture a touch input on, for example, the palm of the user's hand when the palm is the interaction surface. Details of such an embodiment of the sensor 150 are provided in the article "Imaginary Phone: Learning Imaginary Interfaces by Transferring Spatial Memory from a Familiar Device," by Sean Gustafson, et al., UIST'11, Oct. 16-19, 2011, pp. 283-292, which is incorporated herein by reference in its entirety.

The sensors described above are not intended to be limiting in any way. Other types of sensors that are configured to sense an input by a user on a skin surface may also be used in embodiments of the present invention.

Figure 3:
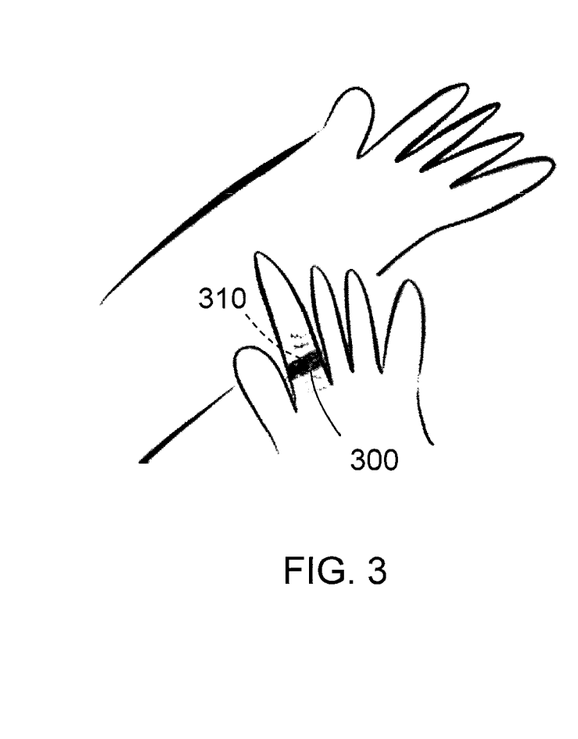
FIG. 3 schematically illustrates an embodiment of a haptic output device of the system of FIG. 1.

FIG. 3 illustrates an embodiment of a wearable device 300 that includes a haptic output device 310 that may be used as the haptic output device 160 of the system of FIG. 1. In an embodiment, the wearable device 300 may be in the form of a ring that is configured to be worn by the user on the finger that interacts with the skin surface that is used as an interactive pad to provide an input to the system 100. The wearable device 300 may provide haptic feedback or a haptic effect to the user as the user's finger touches the skin surface. A haptic effect in the form or a vibration or squeezing motion may be generated by the haptic output device 310 carried by the wearable device 300. In an embodiment, the haptic output device 310 may include or be in the form of an actuator, such as one of the actuators described above.

The haptic feedback may be applied near the contact point of the user's finger to the skin surface. For example, the wearable device 300 may be worn near or on the user's fingernail of the interaction finger, or on another part of the interaction finger, as illustrated in FIG. 3. In an embodiment, the wearable device 300 may be in the form of a wristband or bracelet that is worn on the wrist of either the arm carrying the skin surface that is used as the interactive pad or on the arm attached to the interaction finger. The wristband or bracelet may be configured to vibrate or squeeze the wrist in order to provide a haptic effect to the user.

Figure 4:
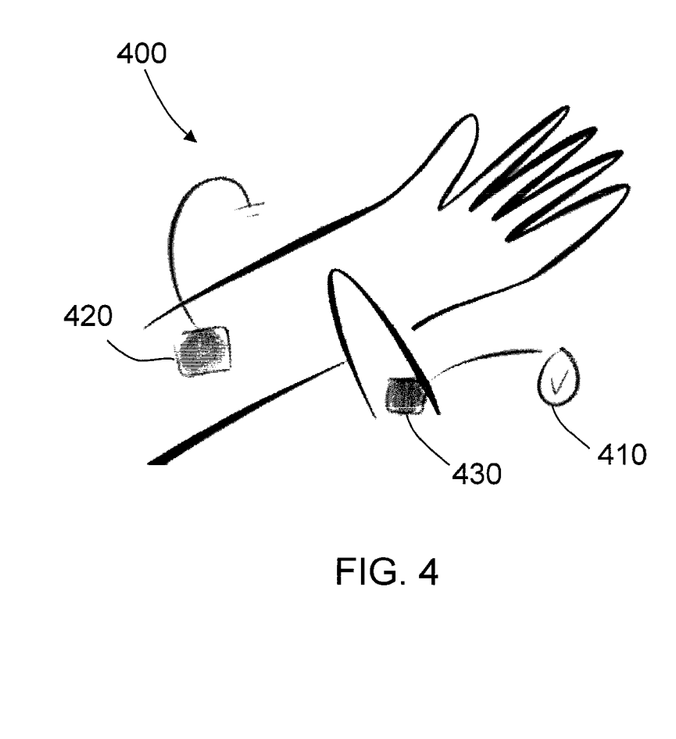
FIG. 4 schematically illustrates an embodiment of a haptic output device of the system of FIG. 1.

FIG. 4 illustrates a haptic output device 400 that may be used as the haptic output device 160 in the system of FIG. 1. The haptic output device 400 includes a power source 410 that is electrically connected to the user's finger. A skin surface 420 that is used as the interaction surface on which the user provides a gesture as an input to the system 100 is connected to ground. When the interacting finger is electrically connected to the power source 410, and the skin surface 420 that is used as the interaction surface is connected to ground, a current may pass through the skin and cause haptic sensations.

In an embodiment, distinct voltages may be applied to the interacting fingerpad and to the skin surface such that an electrotactile stimulation may be applied upon contact. For example, a first electrode 420 in the form of a wearable patch may be applied to the forearm of the user and a second electrode 430 in the form of a wearable patch may be applied to the user's fingerpad such that the two electrodes 420, 430 are kept at different voltages. When the user's fingerpad is in contact with the user's forearm, the circuit is completed such that a current flows and stimulates the mechanoreceptors in the user's skin. In an embodiment, electrotactile stimulation may be produced by charging only one surface, without grounding the other.

In embodiments of the invention, the haptic output device 160 may include electrodes configured to electrically stimulate a muscle(s) and cause the muscle to contract. For example, when a fingerpad is used as the touch surface, the muscles of the finger may be stimulated to push the fingerpad towards or away from the interacting finger. When the forearm is used as the touch surface, muscle contractions in the forearm may change the stiffness of the touch surface or cause the touch surface to vibrate.

Electrodes may be attached to specific locations on the body in order to stimulate one or more muscles and cause them to contract. The contraction of the muscle may be used to increase the stiffness of the interaction surface. For example, the forearm may be made to stiffen as a fingerpad is pressed against it, thereby producing a haptic effect in the form of tactile feedback. The stiffness may also be varied dynamically to create more complex effects, such as a simulation of a button's physical motion, or to create an effect similar to a vibration. The stiffness may also change with the location to indicate the presence of virtual controls, such as buttons and sliders, or their state (e.g., on or off, sensitive or not).

Muscle contractions caused by the electrodes may also be used to cause motion. For example, the contractions may cause a fingerpad used as an interaction surface to bend and push against an interacting finger. For example, a virtual button pushed against a fingerpad may cause the finger to push back once the action has been registered by the processor and a haptic control signal is applied to a power source connected to the electrode.

The muscle contractions may also cause the skin to stretch, and therefore indirectly change the stiffness of the interaction surface. For example, pulling the thumb away from the hand can cause the thenar eminence or the webbing between the thumb and index finger to stiffen. Similarly, the muscle contractions may cause the skin on the interaction surface to be pulled in a direction. For example, the skin of the wrist may be pulled sideways by bending the wrist.

The techniques used to cause involuntary contraction of a muscle by electrical stimulation are well known in the literature, and are generally referred to as "Electrical Muscle Stimulation" or "Functional Electrical Stimulation." For example, "PossessedHand: techniques for controlling human hands using electrical muscles stimuli," by Emi Tamaki, Takashi Miyaki, and Jun Rekimoto, *Proceedings of the SIGCHI Conference on Human Factors in Computing Systems* (CHI'11), ACM, New York, N.Y., USA, 2011, pp. 543-552, which is incorporated herein by reference in its entirety, and "Muscle-propelled force feedback: bringing force feedback to mobile devices," by Pedro Lopes and Patrick Baudisch, *Proceedings of the SIGCHI Conference on Human Factors in Computing Systems* (CHI'13). ACM, New York, N.Y., USA, 2013, pp. 2577-2580, which is incorporated herein by reference in its entirety, disclose using muscle stimulation to trigger hand and finger movement for human-computer interaction. Such techniques typically involve the application of electrodes at specific locations on the body such that a muscle is caused to contract when a current is applied. The electrodes may be applied to the skin with adhesives, and conductive gel may be used to improve contact with the skin.

Figure 5:
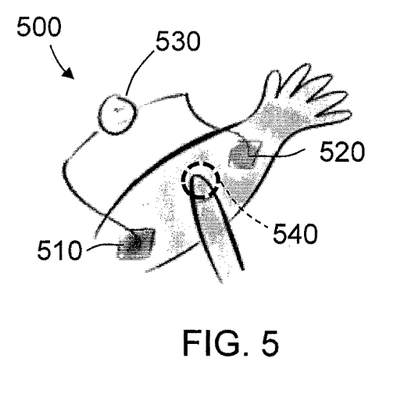
FIG. 5 schematically illustrates an embodiment of a haptic output device of the system of FIG. 1.

FIG. 5 illustrates an embodiment of a haptic output device 500 that may be used as the haptic output device 160 of the system 100 of FIG. 1. The haptic output device 500 includes a first electrode 510 and a second electrode 520 and a power source 530 connected to the first electrode 510 and the second electrode 520. As illustrated, the first electrode 510 and the second electrode 520 are attached to a skin surface on a user's forearm. As the user taps at the location of a virtual button 540 on the forearm, the sensor 150 senses the input and sends an input signal to the processor 110, as described above. The processor 110 determines the haptic effect to be generated based on the input, and sends a haptic control signal to the power source 530, which causes the two electrodes 510, 520 attached to the skin to send an electric pulse to a muscle of the forearm that causes the muscle to stiffen. The haptic effect in the form of the contraction provides confirmation to the user that the button press input is received by the processor 110.

Figures 6, 8:
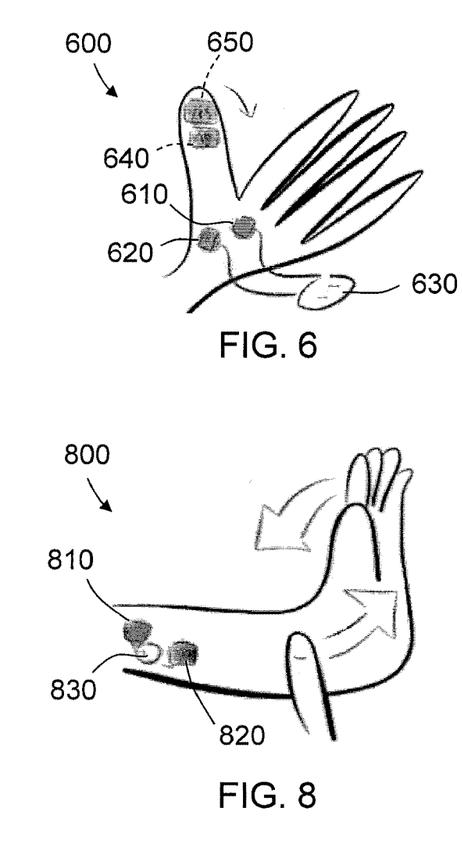
FIG. 6 schematically illustrates an embodiment of a haptic output device of the system of FIG. 1.
FIG. 8 schematically illustrates an embodiment of a haptic output device of the system of FIG. 1.

FIG. 6 illustrates an embodiment of a haptic output device 600 that may be used as the haptic output device 160 of the system 100 of FIG. 1. As illustrated, the haptic output device 600 includes a first electrode 610 and a second electrode 620 connected to a power source 630. The first electrode 610 and the second electrode 620 are located on the user's hand near the base of the thumb, as illustrated. The sensor 150 may be configured to determine which one of two virtual buttons 640, 650 located at the user's thumb, for example, is pressed by the user's index finger of the opposing hand. As one of the virtual buttons 640, 650 is pressed by the user's index finger, the electrodes 610, 620 pass current in the palm in a manner that causes the thumb to moves inwards, thereby giving haptic confirmation feedback to the user that the input was received by the processor 110.

Figure 7:
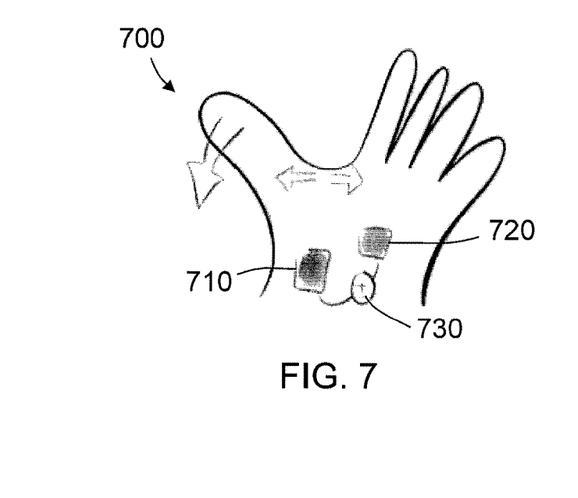
FIG. 7 schematically illustrates an embodiment of a haptic output device of the system of FIG. 1.

FIG. 7 illustrates an embodiment of a haptic output device 700 that may be used as the haptic output device 160 of the system 100 of FIG. 1. As illustrated, the haptic output device 700 includes a first electrode 710 and a second electrode 720 that are connected to a power source 730. The first electrode 710 and the second electrode 720 are located on the palm of the user's hand, as illustrated. In this embodiment, the user may press against the skin between the thumb and index finger to activate a function of the user's phone, for example. As the user presses against the skin, a current flowing between the electrodes 710, 720 may stimulate a muscle that forces the user's thumb to pull away from the hand, thereby stretching the web of skin between the user's thumb and index finger to confirm the user's input.

FIG. 8 illustrates an embodiment of a haptic output device 800 that may be used as the haptic output device 160 of the system 100 of FIG. 1. As illustrated, the haptic output device 800 includes a first electrode 810 and a second electrode 820 that are connected to a power source 830. The first electrode 810 and the second electrode 820 are located on the user's arm, as illustrated. In this embodiment, the user may touch the inner skin of the forearm, near the wrist. As the user presses against the skin, an electric pulse provided to the electrodes 810, 820 may stimulate a muscle that causes the hand to slightly bend backwards. This motion may pull the skin of the wrist towards the hand to provide a directional cue to the user.

As understood by one of ordinary skill in the art, FIGS. 5-8 provide schematic representations of embodiments of the invention, and the locations of the depicted electrodes may not be the precise locations used during implementation. The precise locations of the electrodes will be determined by which muscle is intended to be stimulated by the electrodes for a desired effect.

In accordance with embodiments of the invention, different mechanisms may be used to stretch or pull the skin that is being used as a touch or interaction surface, which may change the stiffness of the surface and produce haptic effects in response to interactions with the skin. For example, increasing the stiffness of the skin may cause the skin to push against the interacting finger. The skin may also be pulled in a direction in order to create perceptible haptic feedback or directional effects. For example, in an embodiment, straps attached to the forearm may be pulled apart to stretch the skin. Such embodiments may use a mechanical apparatus that is configured to deform the skin, and/or other tissues, and cause a change in the interaction surface.

Figure 9:
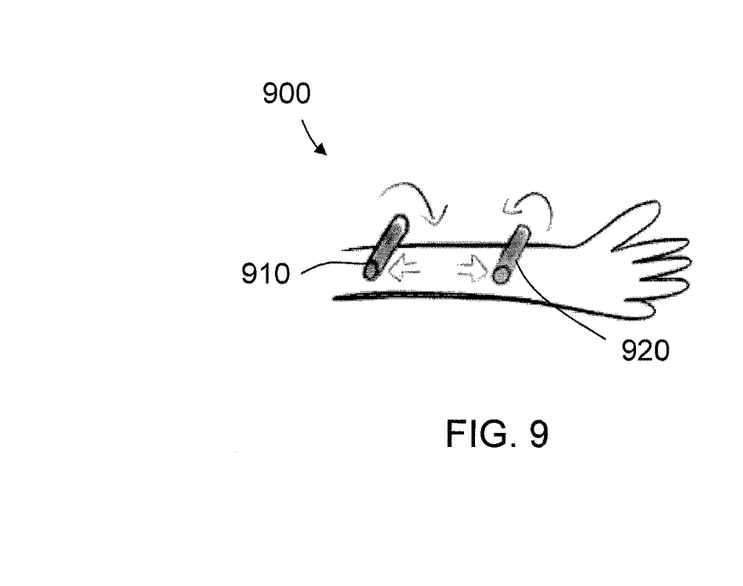
FIG. 9 schematically illustrates an embodiment of a haptic output device of the system of FIG. 1.
Figure 10:
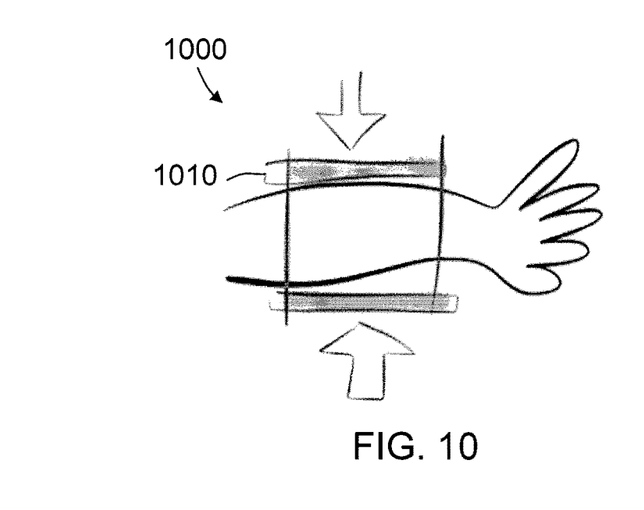
FIG. 10 schematically illustrates an embodiment of a haptic output device of the system of FIG. 1.
Figure 11:
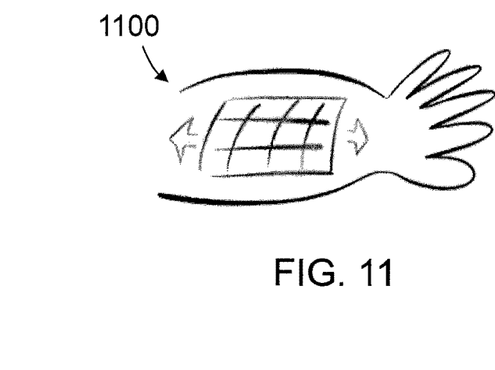
FIG. 11 schematically illustrates an embodiment of a haptic output device of the system of FIG. 1.

For example, as illustrated in FIG. 9, a haptic output device 900 includes a first roller 910 and a second roller 920 that may be attached to the forearm with tight bands, for example, and configured to grab the skin and pull on the skin in opposite directions upon receipt of a haptic control signal from the processor 110. Such a motion by the rollers 910, 920 may make the patch of skin in between the rollers 910, 920 stiffer. FIG. 10 illustrates an embodiment of a haptic output device 1000 that includes an armband 1010 configured to squeeze the sides of the forearm, thereby making the tissue in the forearm bulge or stiffen. FIG. 11 illustrates an embodiment of a haptic output device 1100 that includes a grid of smart material actuators ("SMAs") 1110 that are attached to the skin of the forearm and used to stretch or squeeze the skin of the forearm upon actuation. The grid of SMAs 1110 may be in the form of a haptic tattoo that is applied to the skin surface or otherwise attached to the skin surface by a suitable adhesive. In the embodiments illustrated in FIGS. 9-11, the stimulation generated by the haptic output devices 900, 1000, 1100 may be perceptible on the skin that is used as an interaction surface, and not only on the interacting finger. In some embodiments, the focus of the user on the interaction may be sufficient to give the illusion that the feedback is predominantly on the interacting finger.

Figure 12:
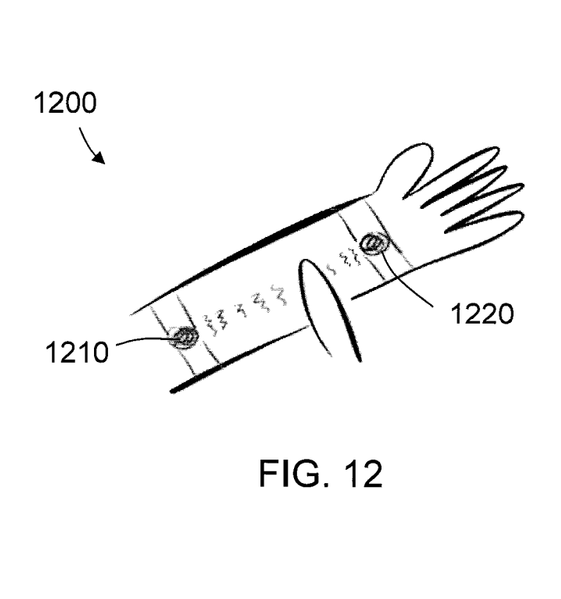
FIG. 12 schematically illustrates an embodiment of a haptic output device of the system of FIG. 1.

In embodiments of the invention, vibrations may be propagated on the skin used as a touch surface. A vibration actuator may, for example, be attached directly to the skin, or even closer to a bone that may have better conduction properties. FIG. 12 illustrated an embodiment of a haptic output device 1200 that includes a first actuator 1210 configured to generate vibrations, and a second actuator 1220 configured to generate vibrations. Each actuator 1210, 1220 is attached to the arm of the user in the periphery of the interaction surface. As the user touches the interaction surface in between the actuators 1210, 1220, the actuators 1210, 1220 may be activated to propagate vibrations to the interacting finger at the contact point on the interaction surface. Such vibrations should ideally not be felt by the skin of the interaction surface. The properties of the vibration may be set such that the vibrations are perceptible mostly by the interacting finger, and not by the interaction surface. For example, the frequency and amplitude of the vibration may be tuned such that the vibrations are barely perceptible on the forearm but obvious to the interacting finger, due to difference in tactile sensitivity. In most cases, however, the vibrations are likely to be felt both on the skin of the interaction surface and on the fingerpad, but the focus of the user on the interaction may still cause the sensation to be predominantly associated with the interacting finger.

Figure 13:
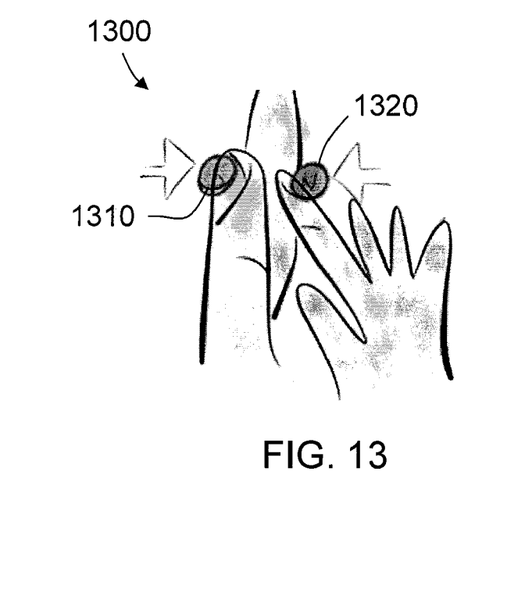
FIG. 13 schematically illustrates an embodiment of a haptic output device of the system of FIG. 1.

In embodiments of the invention, the haptic output device 160 may be configured to generate magnetic forces that may be used to attract or repulse the interacting finger as it touches the touch-sensitive skin surface. For example, the haptic output device 160 may include electromagnets that are configured to cause attraction or repulsion. In an embodiment in which the sensor 150 includes FingerPad, described above, the apparatus attached to the two fingers may be augmented with electromagnets such that the interaction surface can attract or repulse the interacting finger. FIG. 13 illustrates an embodiment of a haptic output device 1300 that includes a first electromagnet 1310 configured to be attached behind a thumb that is used as an interaction surface, and a second electromagnet 1320 that has an opposite polarity as the first electromagnet 1310 and is attached to an index finger of the same or other hand. As the index finger approaches the thumb, the electromagnets 1310, 1320 may be activated such that the user feels an attraction force.

As described above, the touch-sensitive skin surface may feel the haptic feedback that is intended for the interacting finger. In embodiments of the invention, the skin surface may be numbed so that the haptic feedback is attenuated and the skin surface acting as a touch pad does not feel haptic feedback intended for the interacting finger. Vibration feedback may, for example, be masked by producing vibrations to which the forearm adapts over time and no longer feels. This may be done by stimulating the skin prior to the touch input and causing adaptation to the stimuli. In an embodiment, the temperature on the skin may be reduced with Peltier cells, for example, in order to reduce the skin's sensitivity to haptic effects. In an embodiment, chemicals may be used to numb the skin or reduce the skin's sensitivity to haptic effects, although the user may feel the skin's numbness as a haptic effect. Unless the numbness is the intended haptic effect, the numbness sensation should be sustained and therefore quickly fade to the background.

Figure 14:
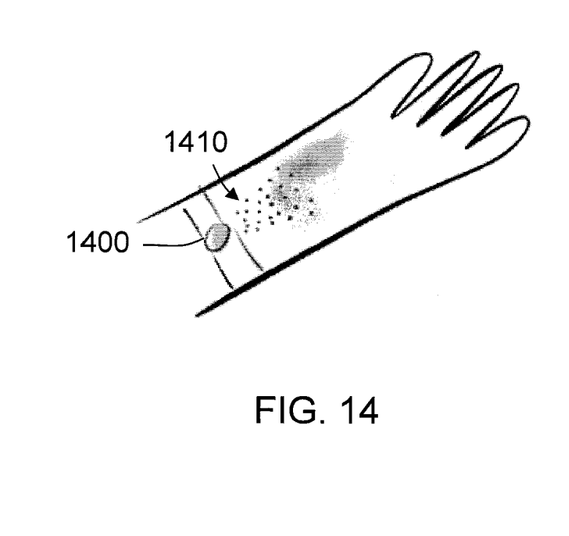
FIG. 14 schematically illustrates an embodiment of a haptic output device of the system of FIG. 1.
Figure 15:
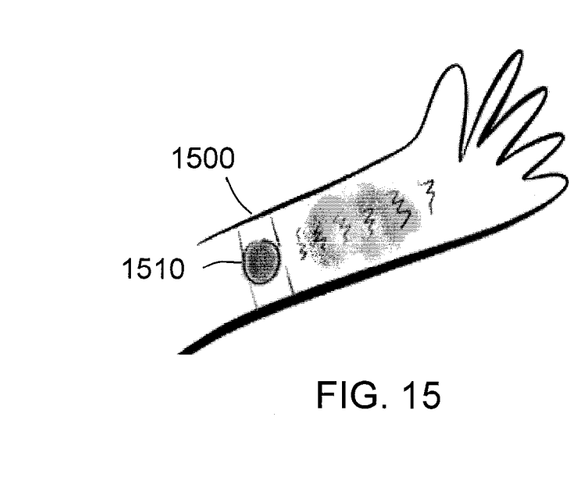
FIG. 15 schematically illustrates an embodiment of a haptic output device of the system of FIG. 1.

FIG. 14 illustrates an embodiment in which a wristband 1400 is configured to spray a topical anesthetic 1410 before interactions begin. The skin is then numbed and does not feel haptic feedback intended for the interacting finger. FIG. 15 illustrates a wristband 1500 that includes an actuator 1510 configured to generate vibrations such that the wristband vibrates for a period a time prior to interactions, thereby causing the skin to adapt to the vibration.

Figure 16:
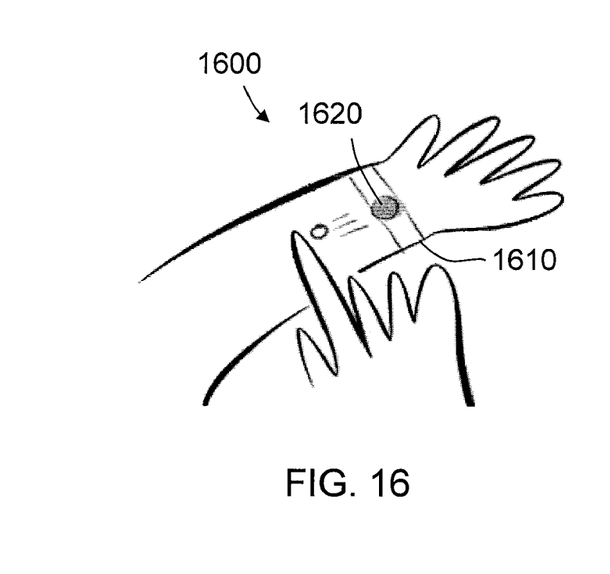
FIG. 16 schematically illustrates an embodiment of a haptic output device of the system of FIG. 1.

In embodiments of the invention, the haptic output device 160 may be configured to project ultrasound or vortices of air towards the interacting finger. In an embodiment in which the sensor 150 includes SenSkin, described above, at least one of the armbands may be configured to project vortices of air in between the two armbands used to capture touch inputs, and therefore cause haptic feedback on the finger. FIG. 16 illustrates a haptic output device 1600 that includes a wristband 1610 that includes an air cannon 1620 that is configured to generate air vortices that may be projected away from the wristband 1610. As the user presses a virtual button on the interaction surface, for example, air vortices may be projected towards the finger to produce confirmation feedback. In an embodiment, the haptic output device 1600 may include a ultrasonic device configured to generate ultrasound.

Figure 17:
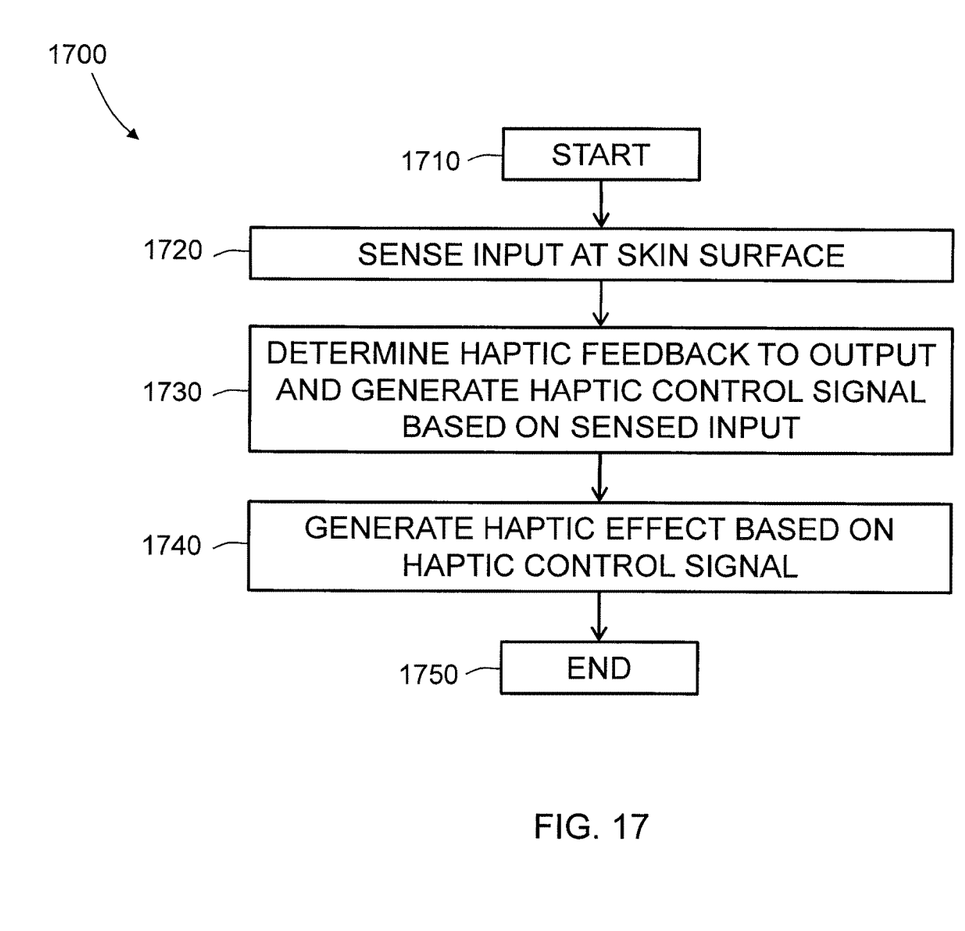
FIG. 17 is a flow chart illustrating a method according to an embodiment of the invention.

FIG. 17 illustrates a method 1700 according to embodiments of the invention. As illustrated, the method 1700 starts at 1710. At 1720, a user of the system 100 described above may use a fingertip to tap, stroke, or otherwise deform a skin surface, such as another fingerpad, a forearm, or a palm of a hand, for example, to provide a touch input, and the touch input is captured or sensed by a sensor, such as one of the sensors described above. In an embodiment, the skin surface that is deformed is carried by the user providing the input. In an embodiment, the skin surface that is deformed is carried by a second user of the system who is different from the user providing the input. The sensor outputs a signal to a processor, such as the processor 110 described above, for processing. At 1730, the processor determines what haptic feedback should be output by a haptic output device, such as one of the haptic output device described above, and generates a haptic control signal based on the sensed touch input captured by the sensor. The processor outputs the haptic control signal to the haptic output device. At 1740, the haptic output device generates a haptic effect based on the haptic control signal. In an embodiment, the haptic effect that is generated is provided to the user carrying the skin surface that was deformed for the input. In an embodiment, the haptic effect is generated to the user providing the input. The haptic effect may be generated to a fingertip or to another body location according to at least one of the embodiments described above. The method 1700 ends at 1750.

The embodiments described herein represent a number of possible implementations and examples and are not intended to necessarily limit the present disclosure to any specific embodiments. Although embodiments described above generally apply to using skin of a user's forearm, thumb, finger, or palm of a hand, for example, as the interaction surface, other skin surfaces may be used, such as ears and earlobes, as described in the article "EarPut: Augmenting Behind-the-Ear Devices for Ear-based Interaction" by Roman Lisserman, et al., *CHI* 2013 *Extended Abstracts*, Apr. 27-May 2, 2013, Paris France, pp. 1323-1328, which is incorporated herein by reference in its entirety, parts of the face such as the forehead and cheeks, as described in the article "Exploring the Use of Hand-to-Face Input for Interacting with Head-Worn Displays" by Marcos Serrano, et al., *CHI* 2014, Apr. 26-May 1, 2014, Toronto, Canada, pp. 3181-3190, which is incorporated herein by reference in its entirety, etc.

In addition, as noted above, the system may be used by a single user or multiple users. For example, in an embodiment, a user of embodiments of the system described above may provide the input using his/her own skin surface or the user may provide the input using another person's skin surface. Similarly, the haptic effect that is generated may be provided to the user providing the input or to another person. For example, in an embodiment, a doctor or surgeon may use a skin surface of a patient's body to provide input to interact with a computer system, for example a computer system that projects information directly onto the patient's body. Haptic effects may be provided to the doctor and/or the patient.

Various modifications can be made to these embodiments as would be understood by one of ordinary skill in the art. Any such modifications are intended to be included within the spirit and scope of the present disclosure and protected by the following claims.

What is claimed is:

1. A system comprising:
a sensor configured to sense a touch input between different skin surface portions;
a processor configured to receive an output signal from the sensor in response to the sensor sensing the touch input between the different skin surface portions, and to generate a haptic control signal based on the output signal; and
a haptic output device configured to generate a haptic effect based on the haptic control signal, the haptic effect being related to the touch input sensed by the sensor between the different skin surface portions.

2. The system according to claim 1, wherein the sensor is configured to sense the touch input between the different skin surface portions, and wherein the haptic output device is configured to generate the haptic effect to the user of the system.

3. The system according to claim 1, wherein the haptic output device is configured to be carried by a wearable device.

4. The system according to claim 3, wherein the wearable device comprises a ring.

5. The system according to claim 3, wherein the wearable device comprises a wristband or a bracelet.

6. The system according to claim 1, wherein the haptic output device comprises an actuator and the haptic effect comprises a vibration.

7. The system according to claim 1, wherein the haptic output device comprises at least one electrode connected to a power source.

8. The system according to claim 7, wherein the haptic effect comprises an electrotactile stimulation.

9. The system according to claim 7, wherein the haptic effect comprises muscle stimulation.

10. The system according to claim 1, wherein the haptic output device comprises a mechanical apparatus configured to stretch or pull the skin.

11. The system according to claim 1, wherein the haptic output device comprises a pair of electromagnets configured to cause attraction or repulsion of two interacting skin surfaces.

12. The system according to claim 1, wherein the haptic output device is configured to generate ultrasound or air vortices.

13. A method comprising:
sensing a touch input between different skin surface portions;
generating a haptic control signal based on the sensed touch input in response to the sensor sensing a touch input between the different skin surface portions; and
generating a haptic effect with a haptic output device based on the haptic control signal, the haptic effect being related to the touch input sensed by the sensor between the different skin surface portions.

14. The method according to claim 13, wherein the haptic effect comprises a vibration.

15. The method according to claim 13, wherein the haptic effect comprises an electrotactile stimulation.

16. The method according to claim 13, wherein the haptic effect comprises muscle stimulation.

17. The method according to claim 13, wherein the haptic effect comprises stretching or pulling the skin.

18. The method according to claim 13, wherein the haptic effect comprises causing attraction or repulsion of two interacting skin surfaces.

19. The method according to claim 13, wherein the haptic effect comprises ultrasound or air vortices.

20. The method according to claim 13, further comprising reducing a sensitivity of the skin surface to the haptic effect.

21. A method comprising:
sensing a touch input at a skin surface;
generating a haptic control signal based on the touch input;
generating a haptic effect with a haptic output device based on the haptic control signal; and
reducing a sensitivity of the skin surface to the haptic effect;
wherein the sensitivity of the skin surface is reduced by applying a topical anesthetic to the skin surface before sensing the touch input.

22. A method comprising:
sensing a touch input at a skin surface;
generating a haptic control signal based on the touch input;
generating a haptic effect with a haptic output device based on haptic control signal; and
reducing a sensitivity of the skin surface to the haptic effect;
wherein the sensitivity of the skin surface is reduced by lowering the temperature of the skin surface.

23. A method comprising:
sensing a touch input at a skin surface;
generating a haptic control signal based on the touch input;
generating a haptic effect with a haptic output device based on the haptic control signal; and
reducing a sensitivity of the skin surface to the haptic effect;
wherein the sensitivity of the skin surface is reduced by applying vibrations to the skin surface before sensing the touch input.

\* \* \* \* \*